(12) United States Patent
Brain et al.

(10) Patent No.: US 6,958,331 B1
(45) Date of Patent: Oct. 25, 2005

(54) BRADYKININ RECEPTOR ANTAGONISTS

(75) Inventors: Christopher Thomas Brain, London (GB); William Cantrell, San Antonio, TX (US); Andrew James Culshaw, London (GB); Edward Karol Dziadulewicz, London (GB); Terance William Hart, London (GB); Timothy John Ritchie, London (GB); Liladhar Waykole, Succasunna, NJ (US)

(73) Assignee: Novartis AG, Basel (CH)

( * ) Notice: Subject to any disclaimer, the term of this patent is extended or adjusted under 35 U.S.C. 154(b) by 210 days.

(21) Appl. No.: 10/009,009

(22) PCT Filed: Jun. 2, 2000

(86) PCT No.: PCT/EP00/05059

§ 371 (c)(1),
(2), (4) Date: Dec. 20, 2001

(87) PCT Pub. No.: WO00/75107

PCT Pub. Date: Dec. 14, 2000

(30) Foreign Application Priority Data

Jun. 4, 1999 (GB) .............................................. 9913079

(51) Int. Cl.⁷ .................. C07D 413/14; A61K 31/5377; A61P 25/04
(52) U.S. Cl. ................ 514/227.8; 514/235.5; 514/235.8; 514/252.11; 514/253.01; 514/253.11; 514/318; 514/330; 514/603; 544/60; 544/121; 544/124; 544/129; 544/160; 544/360; 544/364; 546/193; 546/194; 546/225; 546/226; 564/86
(58) Field of Search .......................... 544/60, 121, 124, 544/129, 160, 360, 364; 546/193, 194, 225, 226; 564/86; 514/227.8, 235.5, 235.8, 252.11, 253.01, 253.11, 318, 330, 603

(56) References Cited

U.S. PATENT DOCUMENTS 6,100,278 A    8/2000  Ferrari et al. ............... 514/314

FOREIGN PATENT DOCUMENTS

WO    WO 97/25315    7/1997

OTHER PUBLICATIONS

Marceau F, Hess JF, Bachvarov DR, "The B1 receptors for kinins", Pharmacol Rev. Sep. 1998;50(3):357–86.*

Streitwieser, A. and Heathcock, C.H., "Introduction to Organic Chemistry, 2nd Ed.", Macmillan, New York, 1981, p. 515.*

* cited by examiner

*Primary Examiner*—Mukund J. Shah
*Assistant Examiner*—Thomas McKenzie
(74) *Attorney, Agent, or Firm*—Joseph J. Borovian; E. Jay Wilusz

(57) ABSTRACT

The invention relates to sulfonyl amine derivatives of formula IA

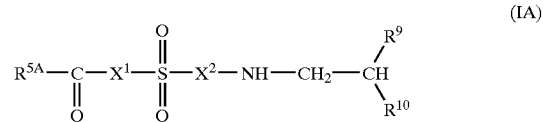

wherein $R^{5A}$, $X^1$, $X^2$, $R^9$ and $R^{10}$ are as defined herein, which derivatives are useful as bradykinin $B_1$ receptor antagonists.

9 Claims, No Drawings

BRADYKININ RECEPTOR ANTAGONISTS

The present invention relates to novel sulfonyl amine derivatives, to processes for their production, their use as pharmaceuticals and to pharmaceutical compositions comprising them. More particularly the present invention provides in a first aspect, a compound of formula IA

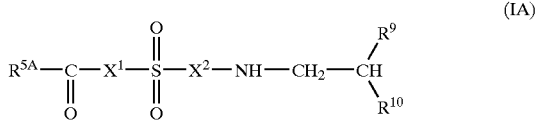
(IA)

wherein
$R^{5A}$ is —$X^4$—$R^{6A}$ or —$N(R^{7A})R^{8A}$, wherein
$X^4$ is piperidinylere or piperazinylene,
$R^{6A}$ is H, $C_1$–$C_4$alkyl, $C_3$–$C_4$alkenyl, $C_3$–$C_4$alkinyl, $C_1$–$C_4$(alkoxyalkyl), $C_1$–$C_4$(carboxyalkyl), a $C_5$–$C_7$heterocyclic group or phenyl$C_1$–$C_4$alkyl;
$R^{7A}$ is amino-$C_2$–$C_4$alkyl or mono- or di-($C_1$–$C_5$alkyl) amino-$C_2$–$C_5$alkyl, and
$R^{8A}$ is H, $C_1$–$C_4$alkyl or has the meanings as given for $R^{7A}$;
$X^1$ is a divalent group of formula IA'

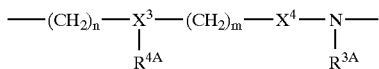

wherein
n is zero or 1:
$X^3$ is CH or N;
(a) $X^4$ is a direct bond, $R^{3A}$ and $R^{4A}$ together are ethylene and m is 2; or
(b) $X^4$ is a direct bond, $R^{3A}$ is H, $C_1$–$C_4$alkyl, $C_3$–$C_6$cycloalkyl, $C_3$–$C_6$alkenyl, $C_3$–$C_6$alkinyl, $C_7$–$C_{10}$aralkyl or $C_6$–$C_9$heteroaralkyl, $R^{4A}$ is H and m is 1 or 2 or 3; or
(c) $X^4$ is —CH($R^{12}$)—, $R^{3A}$ is H and $R^{4A}$ and $R^{12}$ together are propylene and m is 1, or ethylene and m is 2;
$X^2$ is a divalent group of formula IA''

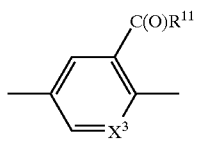

wherein
$X^3$ is CH or N; and
$R^{11}$ is $C_1$–$C_4$alkyl, $C_3$–$C_6$cloalkyl or —$NR^{1A}R^{2A}$, wherein
$R^{1A}$ and $R^{2A}$ independently are $C_1$–$C_4$alkyl or, together with the N-atom to which they are attached, repr s nt a 5 to 7 membered heterocyclic ring; and
$R^9$ and $R^{10}$ independently are a phenyl or pyddine ring; and salts thereof.

It will be understood that the above defined compounds may bear substituents within their stnucture, e.g. may bear appropriate phenyl ring or alkylene moiety substituents, e.g. phenyl and pyridine in the meaning of $R^9$ or $R^{10}$ may be unsubstituted or substituted by one or more halogen, and in the meaning of $R^{3A}$ alkyl may be unsubstituted or substituted by halogen, $C_3$–g$C_6$cycloalkyl or aryl; aralkyl may be unsubstituted or substituted by halogen, methoxy, nitro or $C_1$–$C_4$alkyl which may be unsubstituted or substituted by halogen; heteroaralkyl may be unsubstituted or substituted by $C_1$–$C_4$alkyl. The amino moiety of the defined aminocarbonyl or amide groupings can be any appropriate amino grouping, e.g. cyclic or aliphatic or may bear further substituent groupings.

Even more particularly the present invention provides a 2-(2,2-diphenylethylamino)- -5-(4-aminocarbonyl-piperidine-1-sulfonyl)-benzoic acid amide or -5-(aminocarbonyl-$C_2$–$C_4$alkyleneaminosulfonyl)benzoic acid amide, or salt thereof.

Preferred compounds in accordance with the invention are those of formula I

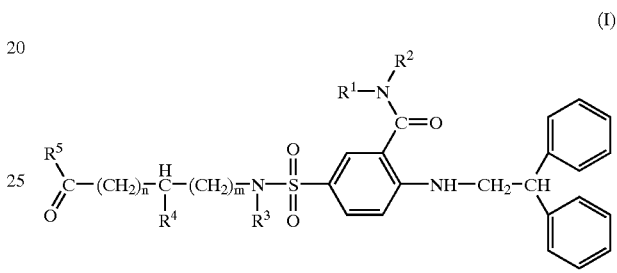
(I)

wherein
$R^1$ and $R^2$ independently are $C_1$–$C_4$alkyl or, together with the N-atom to which they are attached, represent a 5 to 7 membered heterocyclic ring;
(a) $R^3$ and $R^4$ together are ethylene and m is 2; or
(b) $R^3$ is H, $C_1$–$C_4$alkyl, $C_5$–$C_7$cycloalkyl or phenyl-$C_1$–$C_4$alkyl, $R^4$ is H and m is 1 or 2 or 3;
n is zero or 1; and
$R^5$ is —X—$R^6$ or —$N(R^7)R^8$, wherein
X is

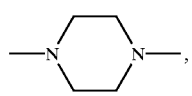

$R^6$ is $C_1$–$C_4$alkyl, $C_3$–$C_4$alkenyl, $C_3$–$C_4$alkinyl, $C_1$–$C_4$(alkoxyalkyl), $C_1$–$C_4$(carboxyalkyl), a $C_5$–$C_7$heterocyclic group or phenyl-$C_1$–$C_4$alkyl;
$R^7$ is amino-$C_2$–$C_4$alkyl or mono- or di-($C_1$–$C_5$alkyl) amino-$C_2$–$C_5$alkyl, and
$R^8$ is H, $C_1$–$C_4$alkyl or has the meanings as given for $R^7$; and salts thereof.

Alkyl groups and moieties in the compounds of formula IA or I may be branched or straight chain. Alkyl groups are suitably straight chain.

Heterocyclic groups may be saturated or unsaturated and may contain one or more additional heterocyclic atoms, e.g. oxygen or sulfur. Examples include piperidin-1-yl, morpholin-1-yl, 3,6-dihydro-2.H.pyridin-1-yl, thiomorpholin-1-yl, pyrrolin-1-yl, morpholin-4-yl, thiomorpholin-4-yl, 3,6-dihydro-2H-pyridin-1-yl, 2,5-dihydropyrrol-1-yl and 4-difluoropiperidin-1-yl, and may be unsubstituted or substituted by one or two halogen atoms.

Compounds of the invention exist in free or salt, e.g. acid addition salt form. The invention is to be understood as including both the compounds of formula IA or I in free as well as in salt form, e.g. as trifluoroacetate or hydrochloride salt. Suitable pharmaceutically acceptable acid addition salts for pharmaceutical use in accordance with the invention include in particular the hydrochloride salt.

In formula IA the following significances are preferred independently, collectively or in any combination or subcombinagon:

(a') $R^{5A}$ is unsubstituted piperazinyl or piperazinyl substituted by methyl, ethyl, benzyl, 2-pyridinyl, methoxyethyl, carboxymethyl or —$CH_2CHCH_2$; or piperidine substituted by methyl;

(a") $R^{5A}$ is $N(R^{7A})R^{8A}$ wherein $R^{7A}$ is aminopropyl, aminobutyl, dimethylaminopropyl, diethylaminopropyl, dibutylaminoethyl, dimethylaminobutyl, or dimethylaminopentyl; and $R^{8A}$ is H, methyl, aminopropyl, aminobutyl, dimethylaminopropyl or dimethylaminobutyl;

(b') $X^1$ is —$(CH_2)_n$—$CH(R^{4A})$—$(CH_2)_2$—$N(R^{3A})$— wherein n is zero or 1 and $R^{3A}$ and $R^{4A}$ together are ethylene;

(b") $X^1$ is —$CH(R^{4A})$—$(CH_2)_m$—$CH(R^{12})$—NH— wherein m is 1 or 2 and $R^{4A}$ and $R^{12}$ together are propylene or ethylene;

(b''') $X^1$ is —$(CH_2)_n$—$CH_2$—$(CH_2)_m$—$N(R^{3A})$— wherein n is zero or 1, m is 1 or 2 or 3 and $R^{3A}$ is H, methyl, isopropyl, isobutyl, fluoroethyl, cyclopropylmethyl, cyclohexylmethyl, cyclobutylmethyl, —$CH(CH_3)C_6H_5$, cyclohexyl, propenyl, butenyl, pentenyl, propinyl, butinyl, pentinyl, benzyl, methylbenzyl, fluorobenzyl, trifluoromethylbenzyl, methoxybenzyl, nitrobenzyl, pyridinylmethyl, methylisoxazolylmethyl, methylthiazolylmethyl or thiophenmethyl;

(c') $X^2$ is a divalent group of formula IA" wherein $X^3$ is CH and $R^{11}$ is methyl, cyclopentyl, cyclohexyl, $N(CH_3)CH_2CH_3$, piperidinyl, morpholinyl, thiomorpholinyl, dihydropyridinyl, dihydropyrrolyl or rdfluoropiperidinyl;

(c") $X^2$ is a divalent group of formula IA" wherein $X^3$ is N and $R^{11}$ is morpholinyl;

(d) $R^9$ and $R^{10}$ are phenyl which is unsubstiuted or substituted by halogen;

(d") $R^9$ is phenyl and $R^{10}$ is pyridine.

In formula I the following significances are preferred independently, collectively or in any combination or subcombination:

(a$^1$) $R^1$ and $R^2$ are independently methyl or ethyl.

(a$^2$) $R^1$ and $R^2$ together with the N-atom to which they are attached are piperidin-1-yl, morpholin-1-yl, 3,6-dihydro-2.H.pyridin-1-yl, thiomorpholin-1-yl or pyrrolin-1-yl.

(b$^1$) $R^3$ and $R^4$ together are ethylene and m is 2.

(b$^2$) $R^3$ is H, methyl, cyclohexyl or benzyl; $R^4$ is H and m is 1 or 2 or 3, especially 1.

(c) n is zero or 1.

(d$^1$) $R^5$ is —X—$R^6$, wherein $R^6$ is $C_1$–$C_4$alkyl (e.g. methyl, ethyl or isopropyl), 3-propenyl, methoxyethyl, carboxymethyl, 2-pyridyl, or benzyl, and X is as defined above.

(d$^2$) $R^5$ is —$N(R^7)R^8$, wherein $R^7$ is aminopropyl, aminobutyl, dipropylaminoethyl, dimethylaminopropyl, dimethylaminobutyl, diethylaminopropyl or dimethylaminopentyl; and $R^8$ is H, methyl, aminopropyl, aminobutyl, dimethylaminopropyl or dimethylaminobutyl.

In addition to the foregoing the present invention also provides a process for the production of a compound of formula IA which process comprises reacting a compound of formula IIA

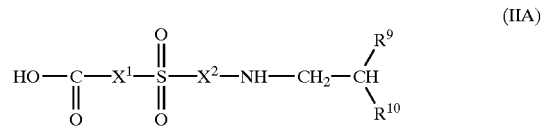

wherein $X^1$, $X^2$, $R^9$ and $R^{10}$ have the meanings given for formula IA, with an amine, e.g. of formula IIIA

wherein $R^{5A}$ has the meanings given for formula IA, and recovering the obtained compound, e.g. of formula IA, in free or in salt form, e.g. add addition salt form.

The present invention also provides a process for the production of a 2-(2,2-diphenylethyl-amino)- -5-(4-aminocarbonylpiperidine-1-sulfonyl)-benzoic acid amide or -5-(aminocarbon-yl-$C_{2-4}$alkylene aminosulfonyl)-benzoic acid amide, for example a compound of formula I as defined above, or salt thereof, which process comprises reacting a 2-(2.2-diphenylethylamino)- -5-(4-carboxy-piperidine-1-sulfonyl)benzoic acid amide or -5-(carboxy-$C_{2-4}$alkylene aminosulfonyl)-benzoic acid amide, for example a compound of formula II

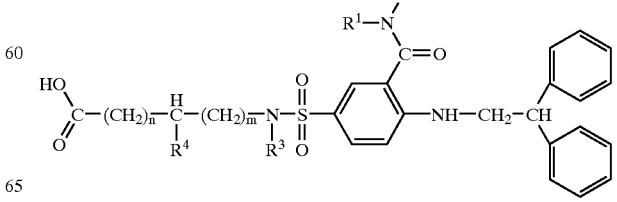

wherein $R^1, R^2, R^3, R^4$, m and n have the meanings given for formula I, with an amine, e.g. of formula III

H—R⁵ (III)

wherein $R^5$ has the meanings given for formula I, and recovering the obtained compound, e.g. of formula I, in free or in salt form, e.g. acid addition salt form.

The reaction may be carried out in accordance with standard procedures, for example by a first acid chloride formation step using e.g. thionyl chloride and catalytic DMF in an inert solvent, e.g. $CH_2Cl_2$, at ambient temperature, followed by the coupling step involving addition of the acid chloride to a mixture of the amine and e.g. TEA, at a temperature of, e.g. −10° C. Aqueous workup followed by precipitation from, e.g. ethyl acetate gives the free base. The salt forms are made by standard procedures known to the skilled artisan.

In the examples the following abbreviations are used: DMF: dimethyl formamide; DMSO: dimethyl sulfoxide; EDTA: ethylenediamine-tetraacefic acid; EtOAc: ethylacetate; IPA: isopropanol; RT: room temperature; TBME: t-butyl methyl ether; TBTU: (O-(benzotriazol-1-yl)-N,N,N', N'-tetramethyluronium tetrafluoroborate; TEA: triethylamine; TFA: trifluoroacetic add; THF: tetrahydrofuran.

EXAMPLE 1

Preparation of {2-(2,2-diphenyl-ethylamino)-5-[4-(4-Isopropyl-piperazine-1-carbonyl)-piperidine-1-sulfonyl]-pheny}-morpholin-4-yl-methanone
(formula I: $R^1+R^2+N$=morpholin-4-yl, $R^3+R^4$=ethylene, m=2, n=zero, $R^5$=4-isopropyl-piperazin-1-yl)

(a) A 5 liter flask is charged with {2-(2,2-diphenyl-ethylamino)-5-[4-(4-carboxy)-piperidine-1-sulfonyl]-phenyl}-morpholin-4-yl-methanone (130.2 g), $CH_2Cl_2$ (1.3 l), DMF (0.82 g) and thionyl chloride (18.1 ml, 29.51 g). The suspension is stirred at ambient temperature (the solids dissolved after ~2 h). The volatiles are removed by rotary evaporation (30° C., house vacuum) and the crude acid chloride is redissolved in $CH_2Cl_2$ (300 ml). The solution of acid chloride is added to a mixture of isopropylpiperazine (47.60 g), TEA (98.09 g) and $CH_2Cl_2$ (1 l) at −10° C. over 1 h. The reaction is worked up by removing volatiles via rotary evaportion. The residue is suspended in EtOAc (2.0 l) and washed with water (2×500 ml), brine (500 ml) and dried ($Na_2SO_4$). The volume is reduced by rotary evaporation (35° C., house vacuum) to ~500 ml and stirred at ambient temperature for 17 h. The suspension is filtered and dried (40° C., house vacuum) to give the title compound as free base.

(b) A 5 liter flask is charged with the above compound (121.3 g), $CH_2Cl_2$ (1.2 l), and 37% HCl (17.38 g). After stirring for 30 min, the volatiles are removed by rotary evaporation and the residue is triturated with IPA (1 l). The suspension is filtered and dried (40° C., house vacuum) to give the crude HCl salt of the title compound.

(c) A 2 liter flask is charged with the above crude HCl salt (133.7 g), silica gel (13.0 g) and $CH_2Cl_2$ (1.3 l). The mixture is stirred for 15 min at ambient temperature and then filtered. This process is repeated twice more. The solvent is removed by rotary evaporation. The residue is suspended in a mixture of IPA (1.0 l) and water (100 ml) and heated to reflux. The solution is allowed to cool to ambient temperature and stir for 17 h. The resulting suspension is filtered and dried. The solid is suspended in acetone (1.0 l) and refluxed for 4.5 h. The suspension is cooled to ambient temperature and stirred for 3 days. The suspension is filtered and dried (60° C., house vacuum, 2 days) to give the title compound as HCl salt.

In the following examples compounds of formula IA wherein $R^{3A}$ and $R^{4A}$ together are ethylene, m is 2, $X^3$ is CH and $R^{5A}$ is —$X^A$—$R^{6A}$ wherein $X^A$ is piperazin-1,4-ylene, are prepared analogously to Example 1:

| Example | $R^{11}$ | n | $R^{6A}$ | $R^9/R^{10}$ |
| --- | --- | --- | --- | --- |
| 2* | morpholin-4-yl | 0 | —$CH_3$ | phenyl |
| 3* | 3,6-dihydro-2H-pyridin-1-yl | 0 | —$CH_3$ | phenyl |
| 4 | piperidin-1-yl | 0 | —$CH_3$ | phenyl |
| 5* | morpholin-4-yl | 0 | —$CH_2CH_3$ | phenyl |
| 6 | thiomorpholin-4-yl | 0 | —$CH_3$ | phenyl |
| 7* | morpholin-4-yl | 0 | benzyl | phenyl |
| 8 | —$N(CH_3)CH_2CH_3$ | 0 | —$CH_3$ | phenyl |
| 9* | morpholin-4-yl | 0 | —$CH_2CHCH_2$ | phenyl |
| 10* | morpholin-4-yl | 0 | —$CH_2CH_2OCH_3$ | phenyl |
| 11* | 3,6-dihydro-2H-pyridin-1-yl | 0 | —$CH(CH_3)CH_3$ | phenyl |
| 12* | morpholin-4-yl | 0 | 2-pyridinyl | phenyl |
| 13 | 2,5-dihydropyrrol-1-yl | 0 | —$CH_3$ | phenyl |
| 14 | 3,6-dihydro-2H-pyridin-1-yl | 1 | —$CH_3$ | phenyl |
| 15 | morpholin-4-yl | 0 | —$CH_2C(O)OH$ | phenyl |
| 1.1 | morpholin-4-yl | 1 | —$CH_3$ | phenyl |
| 1.2 | —$CH_3$ | 0 | —$CH_3$ | phenyl |
| 1.3 | morpholin-4-yl | 0 | —$CH_3$ | 4-Cl-phenyl |
| 1.4 | —$C_5H_9$ | 0 | —$CH_3$ | phenyl |
| 1.5 | —$C_6H_{11}$ | 0 | —$CH_3$ | phenyl |
| 1.6 | morpholin-4-yl | 0 | —$CH_3$ | 4-F-phenyl |
| 1.7 | 4-difluoropiperidin-1-yl | 0 | —$CH_3$ | phenyl |
| 1.8 | morpholin-4-yl | 0 | —H | phenyl |

*as trifluoroacetate

In the following examples compounds of formula I wherein $R^3$ and $R^4$ together are ethylene, m is 2 and $R^5$ is —$N(R^7)R^8$ are prepared analogously to Example 1:

| Example | —NR¹R² | n | R⁷ | R⁸ |
|---|---|---|---|---|
| 16 | 3,6-dihydro-2H-pyridin-1-yl | 0 | —(CH₂)₃N(CH₃)₂ | —(CH₂)₃N(CH₃)₂ |
| 17 | morpholin-4-yl | 0 | —(CH₂)₄NH₂ | —(CH₂)₃NH₂ |
| 18 | morpholin-4-yl | 0 | —(CH₂)₃N(CH₃)₂ | —(CH₂)₄N(CH₃)₂ |
| 19 | morpholin-4-yl | 0 | —(CH₂)₃N(CH₃)₂ | —CH₃ |
| 20 | morpholin-4-yl | 0 | —(CH₂)₃N(CH₂CH₃)₂ | —H |
| 21 | morpholin-4-yl | 0 | —(CH₂)₂N[(CH₂CH(CH₃)₂]₂ | —H |
| 22 | morpholin-4-yl | 0 | —CH₂C(CH₃)₂CH₂N(CH₃)₂ | —H |

In the following examples compounds of formula IA wherein n is 0, m is 2, $X^4$ is a direct bond, $R^{3A}$ and $R^{4A}$ together are ethylene and $R^{11}$ is morpholin-4-yl are prepared analogously to Example 1:

| Example | R⁵ᴬ | X³ | X⁵ | R⁹ | R¹⁰ |
|---|---|---|---|---|---|
| 3.1 | 4-methylpiperazin-1-yl | N | C | phenyl | phenyl |
| 3.2 | 4-methylpiperazin-1-yl | C | N | phenyl | phenyl |
| 3.3 | 1-methyl-piperidin-4-yl | N | C | phenyl | phenyl |
| 3.4 | 4-methylpiperazin-1-yl | C | C | phenyl | pyridine |

In the following examples compounds of formula IA wherein $R^{3A}$ is H, $R^{5A}$ is 4-methylpiperazin-1-yl, $R^9$ and $R^{10}$ are phenyl, $R^{11}$ is morpholin-4-yl, n is 0, $X^3$ and $X^5$ are CH and $X^4$ is —$CH(R^{12})$— are prepared analogously to Example 1:

| Example | R⁴ᴬ + R¹² together | m |
|---|---|---|
| 4.1 | propylene | 1 |
| 4.2 | ethylene | 2 |

In the following examples compounds of formula IA wherein $R^{1A}$ and $R^{2A}$ together with the N-atom to which they are attached are morpholin-4-yl, $R^{4A}$ is H and $R^{5A}$ is —$X^A$—$R^{6A}$ wherein $X^A$ is piperazin-1,4-ylene, are prepared analogously to Example 1:

| Example | R³ᴬ | m | n | R⁶ᴬ |
|---|---|---|---|---|
| 23 | —CH₃ | 1 | 1 | —CH₃ |
| 24* | —CH₃ | 1 | 1 | —CH(CH₃)CH₃ |
| 25* | benzyl | 1 | 0 | —CH₃ |
| 26* | cyclohexyl | 1 | 0 | —CH₃ |
| 27* | —CH₃ | 1 | 0 | —CH(CH₃)CH₃ |
| 28* | benzyl | 1 | 1 | —CH(CH₃)CH₃ |
| 29 | —H | 2 | 1 | —CH(CH₃)CH₃ |
| 30 | —CH₃ | 3 | 1 | —CH₃ |
| 5.1 | —CH₂C₃H₅ | 2 | 0 | —CH₃ |
| 5.2 | 2-methylbenzyl | 2 | 0 | —CH₃ |
| 5.3 | 2-fluorobenzyl | 2 | 0 | —CH₃ |
| 5.4 | 3-methylbenzyl | 2 | 0 | —CH₃ |
| 5.5 | 3-fluorobenzyl | 2 | 0 | —CH₃ |
| 5.6 | 4-methylbenzyl | 2 | 0 | —CH₃ |
| 5.7 | 4-fluorobenzyl | 2 | 0 | —CH₃ |
| 5.8 | —CH₂CH₂F | 2 | 0 | —CH₃ |
| 5.9 | —CH(CH₃)C₆H₅ | 2 | 0 | —CH₃ |
| 5.10 | —CH₂CH(CH₃)₂ | 2 | 0 | —CH₃ |
| 5.11 | —CH₂C(CH₂)CH₃ | 2 | 0 | —CH₃ |
| 5.12 | 2-trifluoromethylbenzyl | 2 | 0 | —CH₃ |
| 5.13 | 3-trifluoromethylbenzyl | 2 | 0 | —CH₃ |
| 5.14 | 4-trifluoromethylbenzyl | 2 | 0 | —CH₃ |
| 5.15 | 3-methoxybenzyl | 2 | 0 | —CH₃ |
| 5.16 | 4-methoxybenzyl | 2 | 0 | —CH₃ |
| 5.17 | 2-nitrobenzyl | 2 | 0 | —CH₃ |
| 5.18 | 3-nitrobenzyl | 2 | 0 | —CH₃ |
| 5.19 | pyridin-3-ylmethyl | 2 | 0 | —CH₃ |
| 5.20 | pyridin-4-ylmethyl | 2 | 0 | —CH₃ |
| 5.21 | —CH₂CHCH₂ | 2 | 0 | —CH₃ |
| 5.22 | —CH₂CCH | 2 | 0 | —CH₃ |
| 5.23 | 5-methylisoxazol-3-ylmethyl | 2 | 0 | —CH₃ |
| 5.24 | 2-methylthiazol-4-ylmethyl | 2 | 0 | —CH₃ |
| 5.25 | —CH₂CHC(CH₃)₂ | 2 | 0 | —CH₃ |
| 5.26 | —CH₂CHCHCH₃ | 2 | 0 | —CH₃ |
| 5.27 | —CH₂C₆H₁₁ | 2 | 0 | —CH₃ |
| 5.28 | —CH₂C₄H₇ | 2 | 0 | —CH₃ |
| 5.29 | —CH₂CCCH₃ | 2 | 0 | —CH₃ |
| 5.30 | thiophen-3-ylmethyl | 2 | 0 | —CH₃ |
| 5.31 | thiophen-2-ylmethyl | 2 | 0 | —CH₃ |
| 5.32 | —CH₂CCCH₂CH₃ | 2 | 0 | —CH₃ |
| 5.33 | —CH(CH₃)₂ | 2 | 0 | —CH₃ |

CHARACTERISING DATA

Compounds of the above tables are found to exhibit the following HPLC retention data [min]:

| No. | [min] |
|---|---|
| 1 | 5.91* |
| 2 | 5.68* |
| 3 | 6.22* |
| 4 | 5.43** |
| 5 | 23.55*** |
| 6 | 5.24** |
| 7 | 25.93*** |
| 8 | 5.09** |
| 9 | 23.98*** |
| 10 | 23.89*** |
| 11 | 6.37* |
| 12 | 23.68*** |
| 13 | 5.10** |
| 14 | 6.17**** |
| 15 | 5.28**** |
| 1.1 | 4.95***** |
| 1.2 | 6.00**** |
| 1.3 | 6.4**** |

-continued

Compounds of the above tables are found to exhibit the following HPLC retention data [min]:

| No. | [min] |
|---|---|
| 1.4 | 6.82**** |
| 1.5 | 7.17**** |
| 1.6 | 5.0***** |
| 1.7 | 5.7***** |
| 16 | 24.03*** |
| 17 | 4.6**** |
| 18 | 20.1*** |
| 19 | 22.6*** |
| 20 | 22.58*** |
| 21 | 27.57*** |
| 22 | 22.9*** |
| 3.1 | 5.03***** |
| 3.2 | 5.8* |
| 3.3 | 5.83* |
| 3.4 | 3.4***** |
| 4.1 | 5.467* |
| 4.2 | 5.822* |
| 23 | 5.57* |
| 24 | 5.9* |
| 25 | 23.82*** |
| 26 | 24.95*** |
| 27 | 5.90* |
| 28 | 6.23* |
| 29 | 5.35* |
| 30 | 5.75* |
| 5.1 | 5.833* |
| 5.2 | 6.367* |
| 5.3 | 6.100* |
| 5.4 | 6.250* |
| 5.5 | 6.167* |
| 5.6 | 6.45* |
| 5.7 | 6.200* |
| 5.8 | 5.467 |
| 5.9 | 6.167* |
| 5.10 | 5.900* |
| 5.11 | 6.338* |
| 5.12 | 6.998* |
| 5.13 | 6.983* |
| 5.14 | 7.03* |
| 5.15 | 6.083* |
| 5.16 | 6.100* |
| 5.17 | 6.067* |
| 5.18 | 5.967* |
| 5.19 | 4.767* |
| 5.20 | 4.667* |
| 5.21 | 5.567* |
| 5.22 | 6.02* |
| 5.23 | 6.138* |
| 5.24 | 6.087* |
| 5.25 | 6.558* |
| 5.26 | 6.382* |
| 5.27 | 6.932* |
| 5.28 | 6.547* |
| 5.29 | 6.26* |
| 5.30 | 6.453* |
| 5.31 | 5.7***** |
| 5.32 | 5.7***** |
| 5.33 | 6.510* |

HPLC conditions:
*: Hypersil 3 micron C 18 BDS column. Gradient elution 10–100% MeCN in water (+0.1% TFA) over 10 min
**: Kingsorb 50 × 4.6 mm C18 column, 3 micron particle size; flow rate 3 ml/min; 90% water (+10 mM NH$_4$OAc 0.3% HCOOH) 10% MeCN to 100% MeCN over 10 min
***: Nucleosil 5 micron C18 column, 25 cm × 4.6 mm. Gradient elution 10–100% MeCN in water (+0.1% TFA) over 40 min
****: Waters Symmetry 3 micron C18 column; 5 × 0.46 cm. Gradient elution 10% to 100% MeCN in water (+0.1% TFA) over 10 min
*****: Kingsorb 3 micron C18 column, 30 × 4.6 mm, gradient elution 10% MeCN in water (+0.1% TFA) to 100% MeCN over 10 min Compounds of formula IIA wherein $X^1$, $R^9$ and $R^{10}$ have the above meanings and $X^2$ is a divalent group of formula

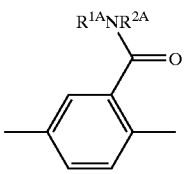

wherein $R^{1A}$ and $R^{2A}$ independently are $C_1$–$C_4$alkyl or, together with the N-atom to which they are attached, represent a 5 to 7 membered heterocyclic ring, may be prepared applying known techniques, e.g. in accordance with the following reaction scheme:

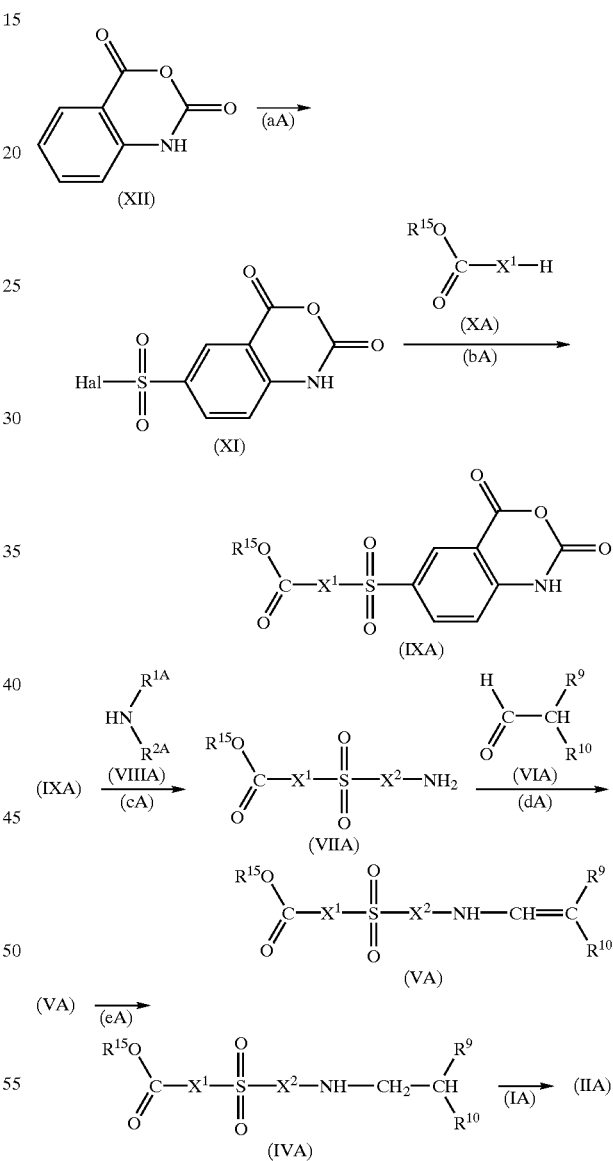

wherein Hal is halogen, e.g. chlorine, $R^{15}$ is $C_1$–$C_4$alkyl, e.g. ethyl, and $X^1$, $X^2$, $R^{1A}$, $R^{2A}$, $R^9$ and $R^{10}$ are as defined for formula IA.

Each of the above reaction steps may be carried out in accordance with conventional procedures as known in the art, e.g. as illustrated in the following examples or analogously thereto. For example in step (aA) the compound of formula XIIA may conveniently be reacted with e.g. chlorosulfonic acid or with chlorosulfonic acid followed by thionyl chloride. In step (bA) the compound of formula XIA may be reacted with the compound of formula XA and e.g. triethylamine in the presence of a solvent like acetonitrile and acetone at 0° C. In step (cA) the compound of formula IXA may be reacted with the compound of formula VIIIA at room temperature in the presence of a solvent like acetonitrile, acetone or ethyl acetate, ethyl acetate being preferred. Preferably an excess of the compound of formula VIIIA may be used, e.g. a 10% excess. In step (dA) the compound of formula VIIA may be reacted with an excess of the compound of formula VIA, e.g. a 10% excess, In the presence of, e.g. trifluoroacetic acid and a desiccant, e.g. trimethyl orthoacetate. The reduction of step (eA) may, e.g. be accomplished via hydrogenation over 10% palladium on carbon in the presence of a solvent, e.g. tetrahydrofuran. The hydrolysis of the ester of formula IVA [step (fA)] may be accomplished in the presence of a base like NaOH, in a solvent like ethanol, methanol, acetone or tetrahydrofuran, preferably tetrahydrofuran. In some of the above steps the reactants may be warmed prior to reaction.

Compounds of formula IIA wherein $X^1$, $R^9$ and $R^{10}$ have the above meanings and $X^2$ is a divalent group of formula

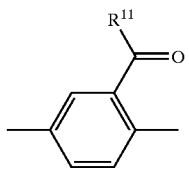

wherein $R^{11}$ is $C_1$–$C_4$alkyl, $C_3$–$C_6$cycloalkyl, may be prepared applying known techniques, e.g. in accordance with the following reaction scheme:

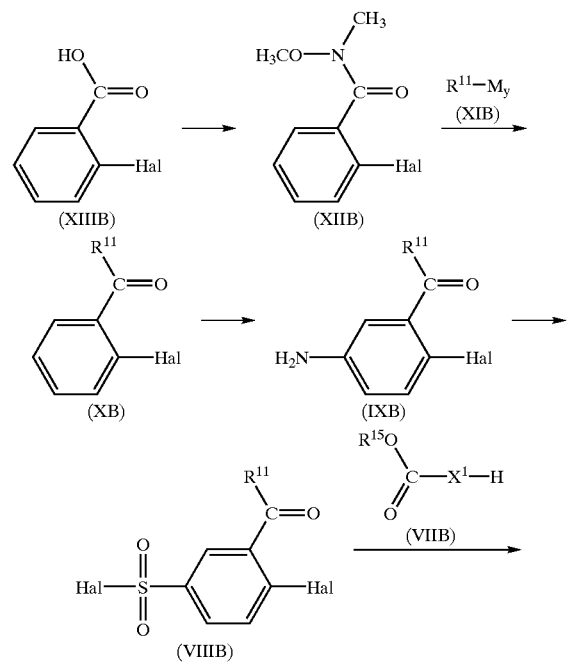

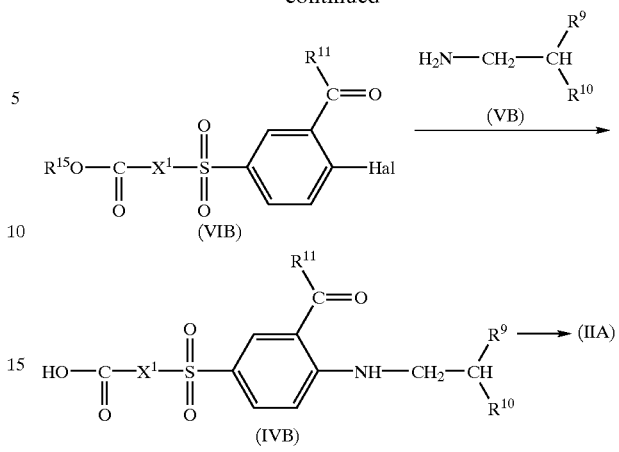

wherein Hal is halogen, e.g. chlorine, $R^{15}$ is $C_1$–$C_4$alkyl, e.g. ethyl, y is 1 and M is a monovalent metal or y is 1/2 and M is a divalent metal, and $X^1$, $R^9$, $R^{10}$ and $R^{11}$ are as defined for formula IA.

Examples of a metal include an alkali metal, e.g. lithium (Li), sodium (Na) and potassium (K), an alkalIne earth metal, e.g. magnesium (Mg), or manganese (Mn), iron (Fe), zinc (Zn) or silver (Ag).

Comrpounds of formula IIA wherein $X^1$, $R^9$ and $R^{10}$ have the above meanings and $X^2$ is a divalent group of formula

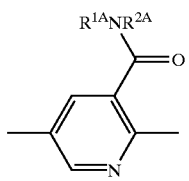

wherein $R^{1A}$ and $R^{2A}$ independently are $C_1$–$C_4$alkyl or, together with the N-atom to which they are attached, represent a 5 to 7 membered heterocyclic ring, may be prepared applying known techniques, e.g. in accordance with the foliowing reaction scheme:

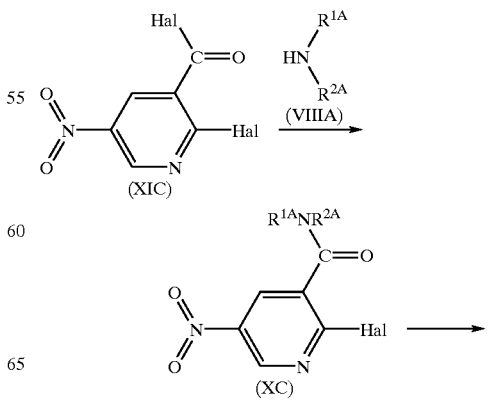

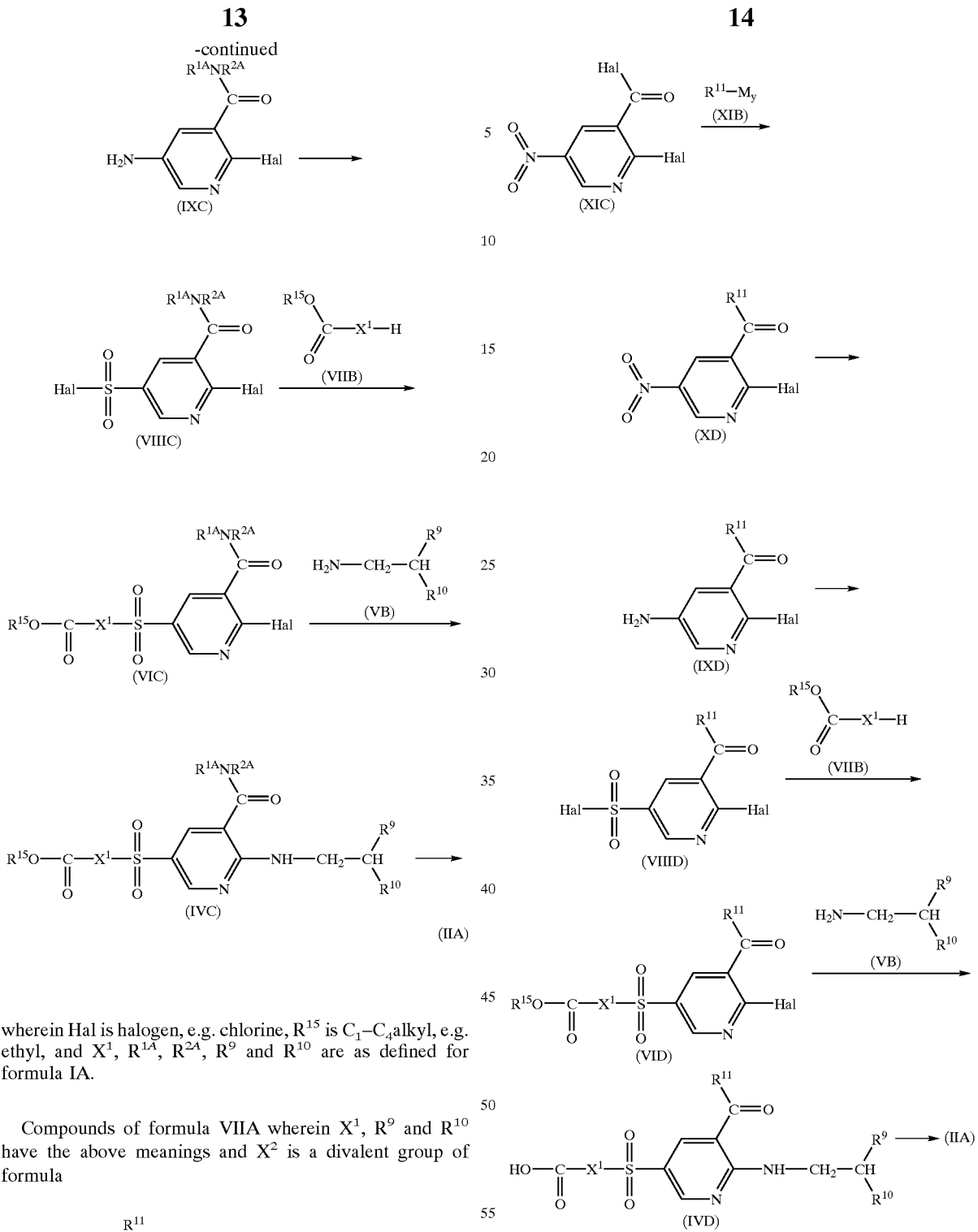

wherein Hal is halogen, e.g. chlorine, $R^{15}$ is $C_1$–$C_4$alkyl, e.g. ethyl, and $X^1$, $R^{1A}$, $R^{2A}$, $R^9$ and $R^{10}$ are as defined for formula IA.

Compounds of formula VIIA wherein $X^1$, $R^9$ and $R^{10}$ have the above meanings and $X^2$ is a divalent group of formula

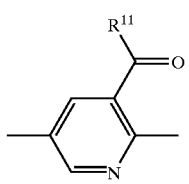

wherein $R^{11}$ is $C_1$–$C_4$alkyl, $C_3$–$C_6$cycloalkyl, may be prepared applying known techniques, e.g. in accordance with the following reaction scheme:

wherein Hal is halogen, e.g. Cl, $R_{15}$ is $C_1$–$C_4$alkyl, e.g. ethyl, y is 1 and M is a monovalent metal or y is 1/2 and M is a divalent metal, and $X^1$, $R^9$, $R^{10}$ and $R^{11}$ are as defined for formula IA.

Compounds of formula II may be prepared app g known techniques, e.g. in accordance with the following reaction scheme:

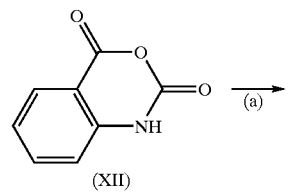
(XII) (a) →
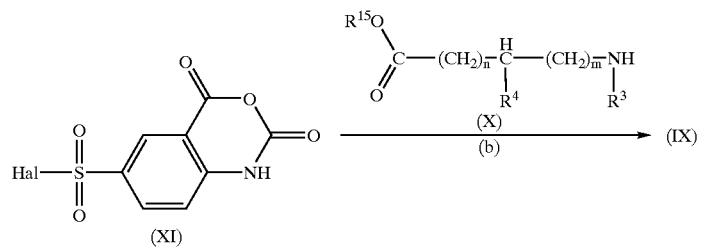
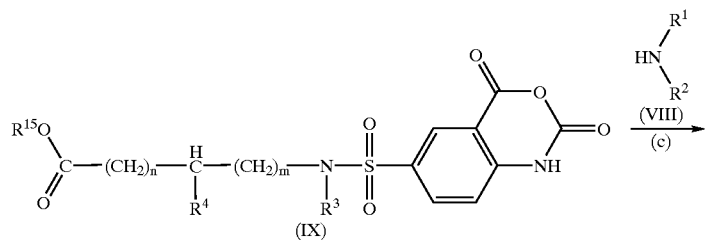
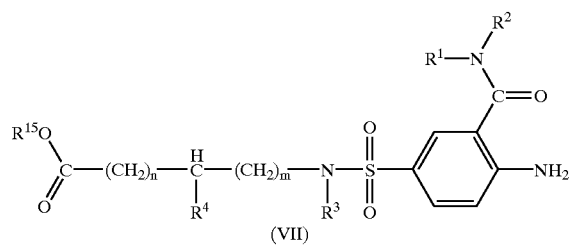
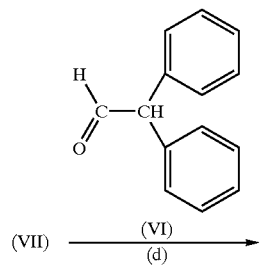
(VII) (VI)/(d) →
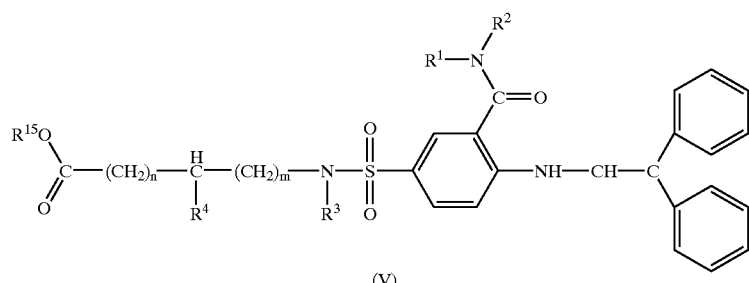
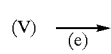

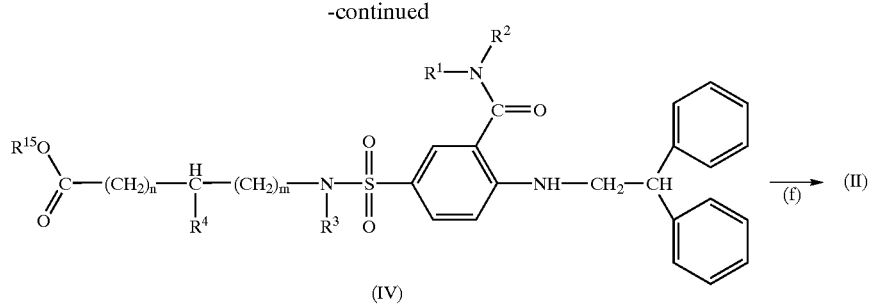

wherein Hal is halogen, e.g. chlorine, $R^{15}$ is $C_1$–$C_4$alkyl, e.g. ethyl, and $R^1$, $R^2$, $R^3$, $R^4$, m and n are as defined for formula I.

Each of the above reaction steps may be carried out in accordance with conventional procedures as known in the art, e.g. as illustrated in the following examples or analogously thereto. For example in step (a) the compound of formula XII may conveniently be reacted with e.g. chlorosulfonic acid or with chlorosulfonic acid followed by thionyl chloride. In step (b) the compound of formula XI is reacted with the compound of formula X and e.g. triethylamine in the presence of a solvent like acetonitrile and acetone at 0° C. In step (c) the sulfonamide of formula IX is reacted with the compound of formula VIII at room temperature in the presence of a solvent like acetonitrile, acetone or ethyl acetate, ethyl acetate being preferred. Preferably an excess of the compound of formula VIII may be used, e.g. a 10% excess. In step (d) the compound of formula VII may be reacted with an excess of the compound of formula VI, e.g. a 10% excess. in the presence of, e.g. trifluoroacetic acid and a desiccant, e.g. trimethyl orthoacetate. The reduction of step (e) may for example be accomplished via hydrogenation over 10% palladium on carbon in the presence of a solvent, e.g. tetrahydrofuran. The hydrolysis of the ester of formula IV [step (f)] may be accomplished in the presence of a base like NaOH, in a solvent like ethanol, methanol, acetone or tetrahydrofuran, preferably tetrahydrofuran. In some of the above steps the reactants may be warmed prior to reaction.

Starting compounds of formula IIIA, VB, VIA, VIB, VIC, VID, VIIB, VIIIA, XA, XIB, XIC and XIIIB are known or may be prepared from corresponding known compounds. Starting compounds III, VI, VIII, X and XII are known or may be prepared from corresponding known compounds.

EXAMPLE S1

Preparation of {2-(2,2-diphenyl-ethylamino)-5-[4-(4-carboxy)-piperldine-1-sulfonyl]phenyl}-morpholin-4-yl-methanone (formula II: $R^1$+$R^2$+N= morpholin-4-yl, $R^3$+$R^4$=ethylene, m=2, n=zero)

(a) A 2 liter flask is charged with isatoic anhydride (180.3 g) and chlorosulfonic acid (367 ml, 643.9 g). The mixture is stirred at ambient temperature for 21 h. Thionyl chloride (80.6 ml, 131.5 g) is added over 2 h and the mixture is stirred at ambient temperature for 16 h. The reaction is worked up by slowly pouring the reaction mixture over ice (4.5 kg) with stirring. The resulting suspension is filtered and the filtercake is washed with water (2×500 ml). The solid is dried (40° C., house vacuum, 48 h) to give compound 2.

(b) A 5 liter flask is charged with 2 (270.2 g) and acetone (2.0 l). The suspension is cooled in an ice/methanol bath and a solution of ethyl isonipecotate (165.7 g) and TEA (156.8 g) in acetone (700 ml) is added over 1.43 h. After the addition is complete, the cooling bath is removed and the mixture is stirred for 2 h. The reaction is worked up by removing volatiles via rotary evaporation (35° C., house vacuum). The solid is triturated with 0.5 N HCl (1763 ml). The suspension is filtered and the filtercake is washed with water (1.0 l). The solid is dried (40° C., house vacuum, 3 days) to give compound 4.

(c) A 12 liter flask is charged with 4 (342.4 g) and EtOAc (3.4 l). A solution of morpholine (85.80 g) in EtOAc (340 ml) is added at ambient temperature over 1.5 h. The mixture is stirred for 30 min. The reaction is worked up by adding charcoal (35.2 g) and filtering through Celite. The solids are washed with EtOAc and the filtrate is reduced to ~2 l by rotary evaporation. Heptane (1.7 l) is added at ambient temperature over 2 h and the resulting suspension is stirred overnight. The suspension is filtered, washed with mother liquor, and dried overnight (40° C., house vacuum) to give 6.

(d) A 12 liter flask is charged with compound 6 (324.7 g) and EtOAc (4.4 l). The mixture is heated until all of the solids dissolved (~35° C.). 2,2-diphenyl ethanal (164.7 g), trimethyl orthoacetate (100.8 g), and TFA (4.35 g) are added and the mixture is stirred at ambient temperature for 3 days. The reaction is worked up by removing EtOAc via rotary evaporator. The residue is triturated with TBME (3.2 l). The resulting suspension is filtered, the filtercake is washed with TBME (320 ml) and dried (40° C., house vacuum, $N_2$ purge) to give compound 8.

(e) A 2.5 liter Parr bottle is charged with compound 8 (118.8 g) and THF (1.2 l). The mixture is heated with stirring until all of the solids are dissolved (~55° C.). Palladium on carbon (10%, anhydrous, 10.47 g) is added and the mixture is shaken under a hydrogen atmosphere (50 psi) at ambient temperature for 24 h. The reaction is worked up by filtering the mixture through Celite. THF is removed by rotary evaporator. The residue is triturated with TBME (1.1 l). The resulting suspension is filtered, the filtercake is washed with TBME (110 ml) and dried (40° C., house vacuum, $N_2$ purge) to give compound 9.

(f) A 12 liter flask is charged with 9 (326.8 g). THF (3.3 l), and 1.0 N NaOH (540 ml). The biphasic solution is stirred at ambient temperature for 24 h. The reaction is worked up by removing THF via rotary evaporator. Water (1.0 l) is added to the remaining aqueous portion and 1.0 N HCl (600 ml) is added with stirring at ambient temperature over 2 h. The resulting suspension is filtered, the filtercake is washed with water (1 l) and dried (40° C., house vacuum, $N_2$ purge) to give the title compound.

Compounds of formula II, IV, V, VII and IX are new and also an embodiment of the present invention.

The following examples for compounds of formula IIA wherein $R^{3A}$ and $R^{4A}$ together are ethylene and m is 2 are prepared analogously to Example S1:

| Example | —NR$^{1A}$R$^{2A}$ | n |
|---------|---------------------|---|
| II.3    | 3,6-dihydro-2H-pyridin-1-yl | 0 |
| II.4    | piperidin-1-yl | 0 |
| II.6    | thiomorpholin-4-yl | 0 |
| II.8    | —N(CH$_3$)CH$_2$CH$_3$ | 0 |
| II.13   | 2,5-dihydropyrrol-1-yl | 0 |
| II.14   | 3,6-dihydro-yl-2H-pyridin-1-yl | 1 |
| II.1.7  | 4-difluoropiperidin-1-yl | 0 |

The following examples for compounds of formula II wherein $R^1$ and $R^2$ together with the N-atom to which they are attached are morpholinyl, and $R^4$ is H are prepared analogously to Example S1:

| Example | R$^3$ | m | n |
|---------|-------|---|---|
| II.23   | CH$_3$ | 1 | 1 |
| II.25   | benzyl | 1 | 0 |
| II.26   | cyclohexyl | 1 | 0 |
| II.27   | —CH$_3$ | 1 | 0 |
| II.28   | benzyl | 1 | 1 |
| II.29   | —H | 2 | 1 |
| II.30   | —CH$_3$ | 3 | 1 |

The compounds of the invention and their pharmaceutically acceptable acid addition salts (hereinafter Pharmaceutical Compounds) have pharmacological acty and are useful as pharmaceuticals. In particular Pharmaceutical Compounds exhibit bradykinin antagonist activity. In particular Pharmaceutical Compounds, e.g. compounds of Example 1 and 2, are active at the human $B_1$ bradykinin receptor.

Bradykinin receptor interaction of the Pharmaceutical Compounds is demonstrated by their ability to displace bradyinin at human bradykinin receptor sites, e.g. as demonstrated in accordance with the following test method.

Test I: Bradykinin Receptor Binding Assay

Cloning of the human bradykinin B1 receptor cDNA: The human bradykinin B1 receptor is cloned from WI38 human foetal lung cell fibroblast cells by expression cloning in *Xenopus laevis oocytes*, which do not express bradykinin B1 receptors normally. A cDNA library is prepared in bacteriophage lambda ZAP express and grown in pools of approximately 10,000 clones per pool. Bacteriophage DNA is prepared from these pools and copy RNA is synthesised with T3 RNA polymerase and after phenol extraction and precipitation, the RNA is injected into *Xenopus oocytes* and allowed to be expressed for 3 days. The oocytes are then assayed electrophysiologically using two electrode voltage clamp, for a response in an endogenous chloride channel that can be activated by endogenous heterotrimeric GTP binding proteins of the Gq/G11 type that can couple to bradykinin receptors. A positive clone is isolated from a positive pool by several stages of splitting the pool into smaller pools and assaying, until a single done is isolated. This cDNA is sequenced and subcloned into pcDNA3 (Clontech) and used to generate a cell-line which expresses the human bradykinin B1 receptor.

Making the HEK cells: The human bradykinin B1 receptor cDNA is subcloned into the Kpn1 and Not1 sites of pcDNA3 (HB1-pcDNA3), is grown up and transfected into human embryonic kidney fibroblast cell line, HEK 293 using the Calcium phosphate method. Cells are grown in Mininum Essential Medium with Eade's Salts (GIBCO) supplemented with 2 mM L-glutamine, 100 units/ml penicillin, 100 μg/ml streptomycin, 1% nonessential amino acids and 10% myodone foetal calf serum (GIBCO) in a humidified atmosphere with 5% $CO_2$ at 37° C.

The 293Hek cells are split 1:2 the day prior to transfection. One 175 cm$^2$ flask with approximately 50% confluent cells is transfected with approximately 30 μg/ml HB1-pcDNA3 DNA using the calcium phosphate precipitate method of transfection. The flask of transfected cells is split 1:3 on day 2 post transfecdon to prevent overgrowth. The following day the cells are split 1:5 and selection in 700 μg/ml G418 begins. The selective medium is changed every 3–4 days. When distinct G418 resistant colonies of transfected cells are seen, approximately 4 weeks after transfection, the cells are cloned by limiting dilution and assayed for binding of [$^3$H]desArg$^{10}$-kallidin. The done with the highest binding is chosen for further use. Care is taken not to allow the cells to overgrow and to maintain G418 in the growth medium.

These HEK 293 cells expressing the human bradykinin $B_1$ receptor are used to prepare membranes. Cells are homogenised in 50 mM Tris-HCl, 1 mM EDTA pH 7.4 at 10,000 rpm for 30 sec in a Potytron homogeniser. All subsequent operations are carried out at 4° C. The resultant suspension is centrifuged for 30 min at 28,000×g. The pellet is washed a further two times by resuspension in Tris-HCl (50 mM, pH 7.4) and recentrifugation. The final pellet is resuspended in Tris-HCl (50 mM, pH 7.4), containing 5% glycerol and frozen rapidly on dry ice in 500 μl aliquots and stored at −80° C.

For use in the binding assay, membranes are thawed, homogenised, and diluted with physiological binding buffer (10 mM HEPES, HBSS {137 mM NaCl, 5.4 mM KCl, 1.3 mM CaCl$_2$, 0.4 mM KH$_2$PO$_4$, 0.3 mM NaHPO$_4$, 0.5 mM MgCl$_2$, 0.4 mM MgSO$_4$, 5.6 mM glucose, pH 7.4} containing 1 mM 1–10 phenanthroline and 0.14 g/l bacitracin. Binding assays are performed in 1.2 ml polypropylene assay tubes (incorporated into a deep well block of 96 or individual iicronics tubes) containing a final volume of 0.5 ml. The assay composition is 425 μl membrane suspension (approximately 20 μg protein per tube) in physiological binding buffer, 50 μl [$^3$H]desArg$^{10}$-kallidin (specific activity 95 Ci/mMol; 6.0±0.5 nM), 25 μl of either DMSO, or unlabelled desArglo kallidin (20 μM) or different concentrations of Pharmaceutical Compounds made up in DMSO. Specific binding to the bradykinin $B_1$ receptor is defined as the difference between that found in total bound tubes and that found in non-specific binding tubes. The reaction is initiated with the addition of membranes and incubated at 4°

C. for 60 min. The reaction is terminated by rapid filtration of the assay mixture through Canberra Packard Unifilter-96 GF/B filterplates (which have been pre-soaked in 0.6% polyethyleneimine for 2 to 3 h at RT). The filters are washed 4 times with 1 ml aliquots of ice cold wash buffer. Mimoscintillant-40 Liquid scintillant is added to the filters and radioactivity bound is determined in a Canberra Packard Topcount scintillation counter. Binding parameters are derived from non-linear iterative curve fitting of three or four data sets simultaneously, using a logistic model in Microcal™ Origin.

$K_1$ values are 0.063 $\mu$M for the peptide antagonist desArg$^{10}$HOE [(D-Arg-[Hyp$^3$, Thi$^5$, D-Tic$^7$, Oic$^8$] desArg$^9$bradykinin)=(D-Arginine-[hydroxyproline$^3$, thienyamine$^5$, D-tetrahydroxyquinoline-3-carboxylic acid$^7$, octahydroindole-2-carboxylic acid$^8$] desArginine$^9$bradykinin)] and in the range of 0.5 nM to 2 $\mu$M for Pharmaceutical Compounds.

Activity specifically as analgesic agents may be demonstrated in accordance with standard test methods, e.g. as described in the following test.

Test II: Thermal Antinociception in Monkeys (Warm Water Tail-witdrawal)

Carrageenan at a dosage of 2 mg in 100 $\mu$l saline is injected subcutaneously into the terminal 1 to 4 cm of the tail of adult rhesus monkeys (Macaca mulatta) folowed by administration of Pharmaceutical Compound in 100 $\mu$l vehicle (0.5% methylcellulose in distilled water) or vehicle to the animal.

The animals are seated in restraint chairs and the lower part of the shaved tail (approximately 15 cm) immersed into warm water maintained at temperatures of 42, 46, and 50° C. Tail-withdrawal latencies are recorded manually by a computerized timer. A maximum cutoff latency (20 sec) is recorded it the subjects fail to remove their tails by this time. A single dosing procedure is used in all test sessions. Each experimental session begins with control determinations at each temperature. Subsequent tail withdrawal latencies are determined based on each experimental condition. The subjects are tested 1 to 2 times at three temperatures in a varying order, with approximately 1 to 2 min interval between tests. Experimental sessions are conducted once per week.

In this test Pharmaceutical Compounds are efficient in preventing or reversing carrageenan-induced hyperalgesia at a dosage in the range of from 0.01 $\mu$Mole/kg to 1 mMole/kg.

Pharmaceutical Compounds are accordingly useful as bradykinin $B_1$ receptor antagonists, e.g. in the treatment of diseases and conditions in which $B_1$ receptor activation plays a role or is implicated. Such conditions indude in particular pain, e.g. bone and pint pain (osteoarthritis), cancer pain, myofascial pain (muscular injury, fibromyalgia) and perioperative pain (general surgery, gynecologic surgery).

Pharmaceutical Compounds are paticularly useful in the treatment or preventon of chronic pain, especially inflammatory, e.g. chronic inflammatory pain, inflammatory diseases for example inflammatory airways disease, e.g. COPD, or in asthma, rhinitis, inflammatory bowel disease, cystitis, e.g. interstitial cystistis, pancreatitis, uveitis, inflammatory skin disorders and rheumatoid arthritis.

Pharmaceutcal Compounds are thus useful as bradykinin $BK_1$ receptor antagonists, e.g. for the treatment of pain of various genesis or aetiology and as anti-inflammatory and/or anti-oedenic agents for the treatment of inflammatory reactions, diseases or conditions, as well as for the treatment of allergic responses mediated by bradykinin. Having regard to their analgesic/anti-inflammatory profile they are useful for the treatment of inflammatory pain, for the treatment of hyperalgesia and, in particular, for the treatment of severe chronic pain. They are, for example, useful for the treatment of pain, inflammation and/or oedema consequential to trauma, e.g. associated with burns, sprains, fracture or the like, subsequent to surgical intervention, e.g. as postoperative analgesics, as well as for the treatment of inflammatory pain of diverse genesis, e.g. for the treatment of osteo and rheumatoid arthritis and rheumatic disease, tenosynovitis and gout. They are further suitable as analgesics for the treatment of pain associated with, e.g., angina, menstriuaton or cancer. As anti-inflammatory/anti-oenema agents, they are further useful, e.g., for the treatment of inflammatory skin disorders, for example psoriasis and eczema.

As bradyidnin BK1 receptor antagonists Pharmaceutical Compounds are also useful as smooth muscle relaxants, e.g. for the treatment of spasm of the gastrointesdinal tract or uterus, e.g. in the therapy of Crohn's disease, ulcerative collitits or pancreatitis.

Pharmaceutca Compounds are in particular useful as agents for the therapy of airways hyperreactivity and for the treatment of inflammatory events associated with airways disease, in particular asthma. In addition, Pharmaceutical Compounds may, for example, be used for the control, restriction or reversal of airways hyperreactivity in asthma.

Inflammatory or obstructive airways diseases to which the present invention is applicable include asthma of whatever type or genesis including both intrinsic and, especially, extrinsic asthma. Thus, Pharmaceutical Compounds are useful for the treatment of allergic asthma, whether atopic (i.e. IgE-mediated) or non-atopic, as well as, for example, exercise induced asthma, occupational asthma, asthma induced following bacterial infection, other non-allergic asthmas and "Wheezy-infant syndrome".

Efficacy in the treatment of asthma will be evidenced by reduced frequency or severity of symptomatic attack, e.g. of acute asthmatic or bronchoconstrictor attack and by reduced requirement for other, symptomatic therapy, for example anti-inflammatory (e.g. corticosteroid) or bronchodilator (e.g. $\beta_2$ adrenergic) therapy.

Inflammatory or obstructive airways diseases to which the present invention is applicable further include pneumnoconlosis (an inflammatory, commonly occupational, disease of the lungs, frequently accompanied by repeated inhalation of dusts) of whatever type or genesis, including, for example, aluminosis, anthracosis, asbestosis, chalicosis, ptilosis, siderosis, sillicosis, tabacosis and, in particular, byssinosis.

Further inflammatory or obstructive airways diseases and conditions for which Pharmaceutical Compounds may be used include adult respiratory distress syndrome (ARDS), chronic obstructive pulmonary or airways disease (COPD or COAD), and bronchitis. Pharmaceutical Compounds may also be used for the treatment of allergic and vasomotor rhinitis.

In addition tothe foregoing Pharmaceutical Compounds are also indicated for use in the therapy of septic shock, e.g.

as anti-hypovolaemic andtor anti-hypotensive agents, in the treatment of inflammatory bowel disease cerebral oedema, headache, migraine and inflammatory skin disease such as eczema and psoriasis, and inflammatory disorders of the gut, e.g. irritable bowel syndrome, Crohn's disease, ulcerative colitis, cystitis, e.g. interstitial cystitis, nephritis, uveitis.

For the above indications the appropriate dosage of Pharmaceutial Compounds will, of course, vary depending upon, for example, the host, the mode of administration and the nature and severity of the condition being treated as well as the relative potency of the particular Pharmaceutical Compound employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 20.0 mg/kg p.o. In humans, an indicated daily dosage is in the range of from about 0.7 to about 1400 mg/day p.o., e.g. from about 50 to 200 mg (70 kg man), conveniently administered once or in divided doses up to 4× per day or in sustained release form. Oral dosage forms accordingly suitably comprise from about 1.75 or 2.0 to about 700 or 1400 mg Pharmaceutical Compound admixed with an appropriate pharmaceuticaly acceptabl diluent or carrier therefor.

Pharmnaceutcal Compounds may alternatively be administered e.g. topically in the form of a cream, gel or the like for example for the treatment of conditions of the sin as hereinbefore described or by inhalation, e.g. in dry powder form, for example for the treatment of asthma.

Examples for compositions comprising Pharmacaubcal Compound include, e.g. a solid dispersion, an aqueous solution, e.g. containing a solubilising agent, e.g. cyclodextrin, a microemulsion and a suspension of, e.g. a micronized hydrochloride salt of a compound of formula IA in, e.g. aqueous methyl cellulose in the range of from 0.1 to 1%, e.g. 0.5%. The composition may be buffered to, e.g. a pH in the range of from 3.5 to 9.5, e.g. to pH 4.5, by a suitable buffer, e.g. malic add.

Pharmaceutical Compounds are also useful as research chemicals.

In accordance with the foregoing the present invention also provides:

(1) A pharmaceutical compound for use as a bradykinin $BK_1$ receptor antagonist, for example for use in any of the particular indications hereinbefore set forth;

(2) A pharmaceutical composition comprising a pharmaceutical compound as under (1) as active ingredient together with a pharmaceutically acceptable diluent or carrier therefor;

(2') A pharmaceutical composition for the treatment or prevehtion of a disease or condition in which bradykinin $B_1$ receptor activation plays a role or is implicated comprising a compound of fomnula IA and a carrier.

(3) A method for the treatment of any of particular indication hereinbefore set forth in a subject in need thereof which comprises administering an effective amount of a pharmaceutical compound as under (1);

(3') A method for treating or preventing a disease or condition in which bradykinin $B_1$ receptor activation plays a role or is implicated comprising administering to a mammal in need thereof a therapeutically effective amount of a compound of formula IA.

(4) Use of a compound of formula IA for the manufacture of a medicament for the treatment or prevention of a disease or condition in which bradykinin B. receptor activation plays a role or is implicated;

(5) A process for the preparation of a compound as under (1).

The preferred Pharmaceutical Compounds for use in accordance with the invention are those of Examples 1 and 2.

What is claimed is:

1. A compound of formula IA

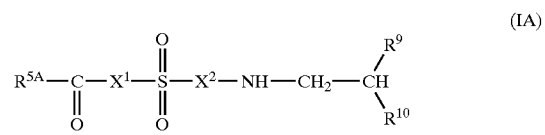

(IA)

wherein
$R^{5A}$ is —$X^A$—$R^{6A}$ or —$N(R^{7A})R^{8A}$, wherein
  $X^A$ is piperidinylene or piperazinylene,
  $R^{6A}$ is H, $C_1$–$C_4$alkyl, $C_3$–$C_4$alkenyl, $C_3$–$C_4$alkinyl, $C_1$–$C_4$(alkoxyalkyl), $C_1$–$C_4$(carboxyalkyl), a $C_5$–$C_7$heterocyclic group or phenyl-$C_1$–$C_4$alkyl;
  $R^{7A}$ is amino-$C_2$–$C_4$alkyl or mono- or di-($C_1$–$C_5$alkyl)amino-$C_2$–$C_5$alkyl, and
  $R^{8A}$ is H, $C_1$–$C_4$alkyl or has the meanings as given for $R^{7A}$;
$X^1$ is a divalent group of formula IA'

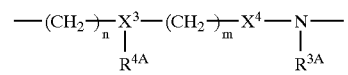

wherein
n is zero or 1;
$X^3$ is CH or N;
(a) $X^4$ is a direct bond, $R^{3A}$ and $R^{4A}$ together are ethylene and m is 2; or
(b) $X^4$ is a direct bond, $R^{3A}$ is H, $C_1$–$C_4$alkyl, $C_3$–$C_6$cycloalkyl, $C_3$–$C_6$alkenyl, $C_3$–$C_6$alkinyl, $C_7$–$C_{10}$aralkyl, or $C_6$–$C_9$heteroaralkyl, $R^{4A}$ is H and m is 1 or 2 or 3; or
(c) $X^4$ is —CH($R^{12}$)—, $R^{3A}$ is H and $R^{4A}$ and $R^{12}$ together are propylene and m is 1, or ethylene and m is 2;
$X^2$ is a divalent group of formula IA"

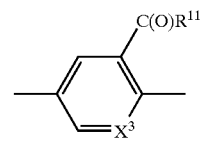

wherein
$X^3$ is CH or N; and
$R^{11}$ is $C_1$–$C_4$alkyl, $C_3$–$C_6$cycloalkyl or —$NR^{1A}R^{2A}$, wherein
  $R^{1A}$ and $R^{2A}$ independently are $C_1$–$C_4$alkyl or, together with the N-atom to which they are attached, represent a 5 to 7 membered heterocyclic ring; and $R^9$ and $R^{10}$ independently are a phenyl or pyridine ring; and salts thereof.

2. A compound of formula I

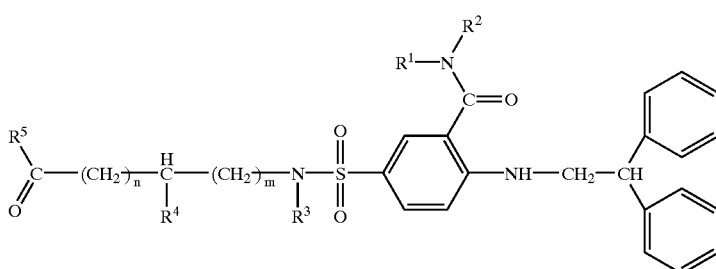

wherein
$R^1$ and $R^2$ independently are $C_1$–$C_4$alkyl or, together with the N-atom to which they are attached, represent a 5 to 7 membered heterocyclic ring;
(a) $R^3$ and $R^4$ together are ethylene and m is 2; or
(b) $R^3$ is H, $C_1$–$C_4$alkyl, $C_5$–$C_7$cycloalkyl or phenyl-$C_1$–$C_4$alkyl, $R^4$ is H and m is 1 or 2 or 3;
n is zero ro 1; and
$R^5$ is —X—$R^6$or —$N(R^7)R^8$, wherein
X is

$R^6$ is $C_1$–$C_4$alkyl, $C_3$–$C_4$alkenyl, $C_3$–$C_4$alkinyl, $C_1$–$C_4$(alkoxyalkyl), $C_1$–$C_4$(carboxyalkyl), a $C_5$–$C_7$heterocyclic group or phenyl-$C_1$–$C_4$alkyl;
$R^7$ is amino-$C_2$–$C_4$alkyl or mono- or di-$(C_1$–$C_5$alkyl)amino-$C_2$–$C_5$alkyl, and
$R^8$ is H, $C_1$–$C_4$alkyl or has the meanings as given for $R^7$;
and salts thereof.

3. A compound according to claim 1 which is {2-(2,2-diphenyl-ethylamino)-5-[4-(4-isopropyl-piperazine-1-carbonyl)-piperidine-1-sulfonyl]-phenyl}-morpholin-4-yl-methanone, or {2-(2,2-diphenyl-ethylamino)-5-[4-(4-methyl-piperazine-1-carbonyl)-piperidine-1-sulfonyl]-phenyl}-morpholin-4-yl-methanone.

4. The compound 2-(2,2-diphenylethylamino)-5-(4-aminocarbonyl-piperidine-1-sulfonyl)benzoic acid amide or a 2-(2,2-diphenylethylamino)-5-(aminocarbonyl-$C_2$–$C_4$alkylene-aminosulfonyl)-benzoic acid amide compound, or a salt of said compounds.

5. A process for preparing a compound of formula IA according to claim 1 which comprises: 1) in a first step, reacting a compound of formula IIA:

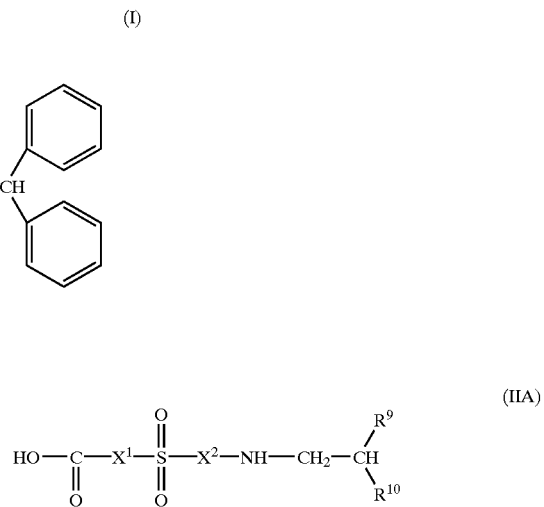

where $X^1$, $X^2$, $R^9$ and $R^{10}$ are as defined in daim 1, with thionyl chloride and a catalytic amount of dimethylformamide to obtain the corresponding acid chloride compound; and 2) in a second step, coupling the acid chloride compound obtained in the first step by adding it to an amine to obtain the desired compound of formula IA in free base or, if desired, salt form.

6. A process for preparing a compound of formula I according to claim 2 which comprises: 1) in a first step, reacting a compound of formula II

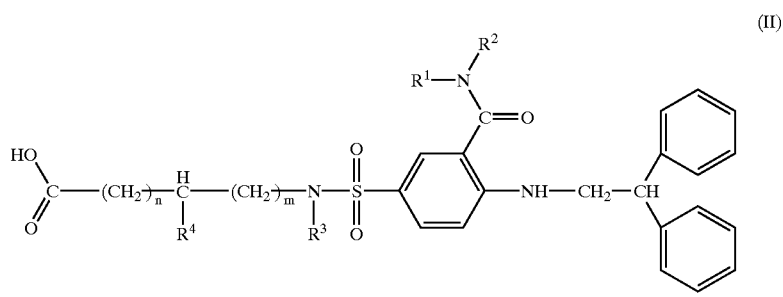

where $R^1$, $R^2$, $R^3$, $R^4$, m and n are as defined in claim 2, with thionyl chloride and a catalytic amount of dimethylformamide to obtain the corresponding acid chloride compound; and 2) in a second step, coupling the acid chloride compound obtained in the first step by adding it to an amine to obtain the desired compound of formula I in free base or, if desired, salt form.

7. A pharmaceutical composition comprising a pharmaceutically acceptable carrier and a therapeutically effective amount of a compound according to claim 1, or a pharmaceutically acceptable salt thereof.

8. A compound having the formula

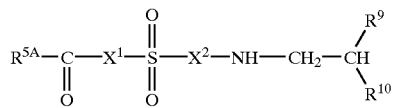

wherein
$R^{5A}$ is $-X^A-R^{6A}$ or $-N(R^{7A})R^{8A}$, wherein
$X^A$ is piperidinylene or piperazinylene,
$R^{6A}$ is H, $C_1$–$C_4$alkyl, $C_3$–$C_4$alkenyl, $C_3$–$C_4$alkinyl, $C_1$–$C_4$(alkoxyalkyl), $C_1$–$C_4$(carboxyalkyl), a $C_5$–$C_7$heterocyclic group or phenyl-$C_1$–$C_4$alkyl;
$R^{7A}$ is amino-$C_2$–$C_4$alkyl or mono- or di-($C_1$–$C_5$alkyl) amino-$C_2$–$C_5$alkyl, and
$R^{8A}$ is H, $C_1$–$C_4$alkyl or has the meanings as given for $R^{7A}$;
$X^1$ is a divalent group of formula IA'

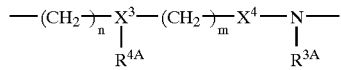

wherein
n is zero or 1;
$X^3$ is CH or N;
(a) $X^4$ is a direct bond, $R^{3A}$ and $R^{4A}$ together are ethylene and m is 2: or
(b) $X^4$ is a direct bond, $R^{3A}$ is H, $C_1$–$C_4$alkyl, which may be unsubstituted or substituted by halogen, $C_3$–$C_6$cycloalkyl or aryl, $C_3$–$C_6$cycloalkyl, $C_3$–$C_6$alkenyl, $C_3$–$C_6$alkinyl, $C_7$–$C_{10}$aralkyl, which may be unsubsbtuted or substituted by halogen, methoxy, nitro or $C_1$–$C_4$alkyl which may be unsubstituted or substituted by halogen, or $C_6$–$C_9$heteroaralkyl, which may be unsubstituted or substituted by $C_1$–$C_4$alkyl, $R^{4A}$ is H and m is 1 or 2 or 3; or
(c) $X^4$ is $-CH(R^{12})-$, $R^{3A}$ is H and $R^{4A}$ and $R^{12}$ together are propylene and m is 1, or ethylene and m is 2;
$X^2$ is a divalent group of formula IA"

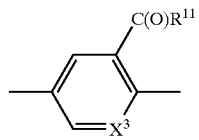

wherein
$X^3$ is CH or N; and
$R^{11}$ is $C_1$–$C_4$alkyl, $C_3$–$C_6$cycloalkyl or $-NR^{1A}R^{2A}$, wherein
$R^{1A}$ and $R^{2A}$ independently are $C_1$–$C_4$alkyl or, together with the N-atom to which they are attached, represent a 5 to 7 membered heterocyclic ring; and
$R^9$ and $R^{10}$ independently are a phenyl or pyridine ring, both of which may be unsubstituted or substituted by one or more halogen atoms;
and salts thereof.

9. A method of treating a condition which is responsive to the antagonism of bradykinin activity selected from the group consisting of pain, inflammatory diseases, inflammatory disorders, edema, spasms and septic shock comprising administering to a mammal in need of such treatment a therapeutically effective amount of a compound according to claim 2, or a pharmaceutically acceptable salt thereof.

* * * * *